(12) United States Patent
Hsu

(10) Patent No.: US 8,145,451 B2
(45) Date of Patent: Mar. 27, 2012

(54) DIGITAL FILTERING SYSTEM, METHOD, AND RECORDING MEDIUM THEREOF

(75) Inventor: Chih-Wei Hsu, Tainan County (TW)

(73) Assignee: Institute for Information Industry, Taipei (TW)

( * ) Notice: Subject to any disclaimer, the term of this patent is extended or adjusted under 35 U.S.C. 154(b) by 621 days.

(21) Appl. No.: 12/333,862

(22) Filed: Dec. 12, 2008

(65) Prior Publication Data

US 2010/0121610 A1    May 13, 2010

(30) Foreign Application Priority Data

Nov. 7, 2008    (TW) ................................ 97143014 A

(51) Int. Cl.
H04B 15/00 (2006.01)
H03M 1/12 (2006.01)
A61B 5/00 (2006.01)

(52) U.S. Cl. .......................... 702/189; 341/155; 600/301

(58) Field of Classification Search .................. 702/189, 702/66, 73, 75–77, 81, 84, 98, 127, 137–139, 702/182–183, 188, 190; 341/126, 155, 157, 341/200; 340/870.18–870.19, 870.2, 870.21, 340/870.25–870.26; 128/900, 920; 600/300–301, 600/561; 703/11–12; 706/16, 25, 34, 38, 706/41, 59–60
See application file for complete search history.

(56) References Cited

U.S. PATENT DOCUMENTS 5,047,930 A * 9/1991 Martens et al. ............... 600/301

* cited by examiner

*Primary Examiner* — Michael Nghiem
*Assistant Examiner* — Toan M Le
(74) *Attorney, Agent, or Firm* — Muncy, Geissler, Olds & Lowe, PLLC

(57) ABSTRACT

A digital filtering system, method, and recording medium thereof are described. In the system, firstly a sensor obtains an analog physiological signal, a quantizing module transforms the physiological signal to a digitalized frequency domain signal, and then a specification parameter module obtains a feature model satisfying the frequency domain signal by matching, for a deciding process module to determine which decision parameter should be used. A filter-Clustering management module starts a relevant filter module according to the matching decision parameter to filter the frequency domain signal. On the contrary, when the frequency domain signal is an abnormal signal, the quantizing module outputs the abnormal signal to a back-end server system. The server system builds more than one updating parameter to update all the decision parameters and feature parameters. Therefore, the decision parameters and the feature parameters are updated on real time, and the physiological signal filtering result is quickly obtained.

28 Claims, 8 Drawing Sheets

DIGITAL FILTERING SYSTEM, METHOD, AND RECORDING MEDIUM THEREOF

CROSS-REFERENCE TO RELATED APPLICATIONS

This application claims the benefit of Taiwan Patent Application No. 097143014, filed on Nov. 7, 2008, which is hereby incorporated by reference for all purposes as if fully set forth herein.

BACKGROUND OF THE INVENTION

1. Field of Invention

The present invention relates to a digital filtering system and a method thereof, and more particularly to a digital filtering system and a method thereof, capable of analyzing physiological signal features, starting the most appropriate filter module, and continuously updating filter module coefficients and decision parameters on real time.

2. Related Art

In the prior art, no manner for which kind of physiological signal inspection operation, the noise filtering is the primarily processed operation.

However, on the market, filters include finite impulse response digital filters, infinite impulse response digital filters, high-pass digital filters, low-pass digital filters, medium frequency digital filters, band pass digital filters, and band rejection digital filters. However, digital filter types, retrieving frequencies, clocks, signal intensities, waveform heights of different physiological signals are different, for example, the physiological signals generated by blood pressure and blood oxygen are different.

Care device manufacturers need to preset care devices or physiological signal measuring devices to the most desired set value before sale. Alternatively, the care personnel continuously adjust the care devices or measuring devices to the set values which are most appropriate for users in a try error manner when using the care devices or measuring devices.

However, the prior art has inevitable disadvantages as follows.

Firstly, the change of the real-time signal cannot be anticipated, no matter how the care devices, the systems, or the measuring devices are optimally set by the people in the industry or the care personnel, as long as the user environment is changed, such as the change of seasons, the placement of appliance devices, or the carrying of portable electronic devices, and the change in the power supply of the electronic device provided with the disposed digital filter, the noise may be generated, such that the accuracy of the measured physiological signal is greatly lowered.

Secondly, the physiological signal is a real-time signal, but the coefficients of most of the digital filters are set to the initially designed ideal value. However, before the digital filter is practically applied to measure the physiological signal, as described above, it is continuously corrected to the most appropriate set value in the manual try error manner, thereby costing a great amount of time and manpower cost. Further, the filters finishing the setting are mostly only applicable to a single user instead of other users, thereby greatly lowering the adaptability of the filter.

Thirdly, electromechanical characteristics (for example, heat noise and circuit magnetic field) generated by an operating circuit of the digital filter may be received by the measuring device due to feedback, such that the noises are mixed in the physiological signal. However, the filter cannot determine whether the electromechanical characteristics are generated by the circuit thereof or not, so the noises generated by the electromechanical characteristics may not be prevented.

SUMMARY OF THE INVENTION

Accordingly, the present invention is directed to a digital filtering system, method, and recording medium thereof, capable of starting a relevant filter according to a type and features of a physiological signal, and correcting filter parameters and feature parameters on real time according to a filtering result.

In order to solve the above system problems, in the technical scheme, the present invention provides a digital filtering system, which includes a sensor, a quantizing module, a specification parameter module, a deciding process module, a filter-Clustering management module, and a server system.

The sensor measures and provides an analog physiological signal. The quantizing module digitalizes and transforms the physiological signal to at least one frequency domain signal. The specification parameter module stores a plurality of feature data for matching with the frequency domain signal modeling a patent into a feature model, so as to build the feature model satisfying (this once is a eigenvector or characteristic vector patent) the frequency domain signal. Or, when the frequency domain signal may not be recognized, the frequency domain signal is considered as an abnormal signal and is output to the server system. The deciding process module stores a plurality of decision parameters, so as to output a matching decision parameter. The filter-Clustering management module starts a relevant filter module according to the matching decision parameter, so as to filter the frequency domain signal. When obtaining the abnormal signal, the server system analyzes the abnormal signal and builds at least one updating parameter, so as to update the feature data and the decision parameters.

In order to solve the method problems, in the technical scheme, the present invention provides a digital filtering method, in which the filtering operation is performed according to the digital filter. Firstly, a sensor obtains at least one analog physiological signal. A quantizing module transforms the physiological signal to at least one frequency domain signal. A specification parameter module matches the frequency domain signal with a plurality of feature data, so as to build a feature model satisfying the frequency domain signal, for a deciding process module to output a matching decision parameter. A filter-Clustering management module starts a relevant filter to filter the frequency domain signal. On the contrary, the frequency domain signal is considered as the abnormal signal, and is transmitted to a server system, such that the server system builds updating parameters according to the abnormal signal, so as to update the decision parameters or the feature data.

The method of the present invention may be realized in form of a computer program product or a non-transitory recording medium. When an electronic device capable of reading the computer program or the recording medium loads the computer program or the record medium, the same problem may be solved by the same method, so as to achieve the same efficacy.

The present invention has the efficacies which may not be achieved by the prior art.

Firstly, the parameters used by the filter module are updated and corrected on real time, so no matter the physiological signal is a signal changed on real time, a signal mixed with the noise, a signal received by the sensor, or a feedback signal (for example, heat noise and electromagnetic wave) generated when the circuit power of the filter is too high, the feature parameters, the decision parameters, and the filter parameters may be generated by the server system and the specification parameter module. Therefore, the signal filtered by the system is the optimum and the most accurate signal.

Secondly, the parameters used by the filter module are updated and corrected on real time, so the electronic device with the same disposed digital filtering system may be applicable to different users, and the digital filtering system is an active waveform recognition digital filtering system, which may be applicable to analyze the physiological signals input by a plurality of different types of sensors at the same time.

Thirdly, the parameters used by the filter module are updated and corrected on real time, so the operation power of the circuit of the digital filtering system may be adjusted. Power adjusting set values are recorded in the decision parameters or the feature parameters, such that if necessary, the circuit power of the digital filtering system is lowered or raised, so as to prevent the noise generated by the circuit of the digital filtering system from being returned and mixed in the physiological signal received by the sensor, thereby improving the accuracy of the physiological signal.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

In order to have a further understanding of the objectives, the structure features, and the functions of the present invention, a detailed description is given as follows with relevant embodiments and accompanying drawings.

Figure 1:
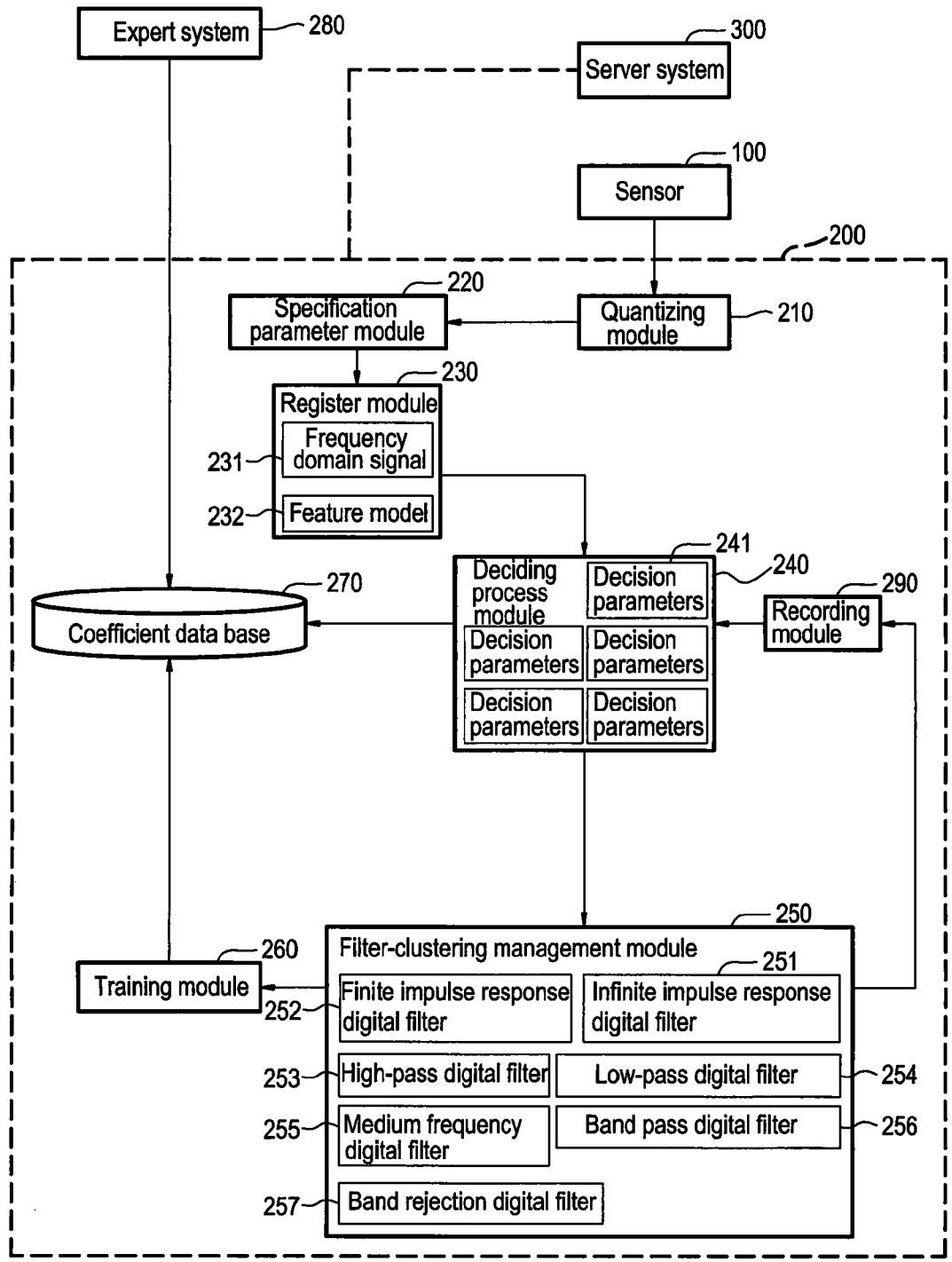
FIG. 1 is a schematic view of a structure of a system according to an embodiment of the present invention.

Referring to FIG. 1, a schematic view of a structure of a system according to an embodiment of the present invention is shown. From a perspective of a block diagram, the digital filtering system includes more than one sensor 100 (one sensor is described in this embodiment), a quantizing module 210, a specification parameter module 220, a deciding process module 240, a filter-Clustering management module 250, and a server system 300.

The sensor 100 may be a blood pressure sensor, a blood oxygen sensor, or a pulse sensor, and is worn on the user's body, for measuring blood pressure, blood oxygen, pulse, or other continuous analog physiological signals of the user.

The quantizing module 210 firstly digitalizes the physiological signal to a digital signal, and then performs a time-frequency transformation on the digitalized physiological signal according to Fourier transform rule, so as to transform the physiological signal to more than one frequency domain signal 231.

The specification parameter module 220 stores a plurality of feature data, and each feature data includes a class data, a waveform data, and a unit parameter. The class data refers to a signal type of the frequency domain signal 231 for matching. The waveform data refers to a shape of the frequency domain signals 231 on a spectrogram, for example, an even harmonic, an odd harmonic, and other double frequency waves. The unit parameter refers to a unit numerical value used by the frequency domain signal 231 on the spectrogram, including a signal retrieving scope, a signal intensity data, a spread spectrum width and density data, and an interval feature data. The signal retrieving scope refers to a specific scope of a setting frequency and around the setting frequency, after different physiological signals are transformed to the frequency domain signals 231. For example, a blood oxygen setting frequency is mostly 20 HZ, and the specific scope is ±3 HZ. For example, a blood pressure setting frequency is 50 HZ or 60 HZ, and the specific scope is ±5 HZ. The signal intensity data refers to a maximum value, a medium value, and a minimum value of the frequency domain signal 231. The spread spectrum width and density data refers to an occupied bandwidth and the density degree of the waveform of the frequency domain signal 231, when the frequency domain signal 231 is spread on the spectrum. The interval feature data refers to a unit data of periodically showing the same waveform by the frequency domain signal 231 in the continuous physiological signal, for example, the waveforms of the physiological signals are the same or similar at every three periodical periods.

The specification parameter module 220 matches the frequency domain signal 231 with all the feature data, so as to obtain at least one feature data by matching and build a feature model 232 of the frequency domain signal 231 according to the feature data. However, when the frequency domain signal 231 does not satisfy any feature data, the specification parameter module 220 judges that the frequency domain signal 231 is an unknown abnormal signal, and outputs the abnormal signal to the server system 300.

In order to prevent the data loss, a register module 230 may be disposed in the digital filtering system 200, so as to record the frequency domain signal 231 and the data of the feature model 232 thereof.

The deciding process module 240 stores a plurality of decision parameters 241, and obtains a matching decision parameter 241 according to the previously built feature model 232. The decision parameters 241 include a filter starting data, for recording the filter module applicable to the frequency domain signal 231; a filter adjusting parameter, being an adjusting parameter used to adjust the started filter module and filter the frequency domain parameter; and an operation power adjusting parameter, for adjusting a power of an operating circuit of the digital filtering system 200. The circuit power of the digital filtering system 200 is adjusted since that the operation circuit may generate the heat noise, the electromagnetic wave, the magnetic field gain, or other electrical characteristics due to the excessively high power, and the electrical characteristics are returned and received by the sensor, so as to be mixed in the measured physiological signal. In this manner, the power of the operating circuit must be lowered.

The filter-Clustering management module 250 includes a plurality of filter modules, mainly starts a filter module according to the matching decision parameter 241, and at the same time adjusts the adjusting parameter of the filter module. The started and adjusted filter module filters the frequency domain signal 231. The filter module may be a finite impulse response digital filter 252, an infinite impulse response digital filter 251, a high-pass digital filter 253, a low-pass digital filter 254, a medium frequency digital filter 255, a band pass digital filter 256, and a band rejection digital filter 257. The filter adjusting parameter is a high-pass parameter, a low-pass parameter, a band pass parameter, or a band rejection parameter and the like, so the setting is performed according to the applicable filter module or by guiding in the relevant filter adjusting parameter.

After the server system 300 obtained the abnormal signal, the server system 300 analyzes the abnormal signal to build at least one updating parameter, then returns to the specification parameter module 220 to update the feature data, and returns to the deciding process module 240 to update the decision parameters 241. However, the server system 300 may pre-stores a plurality of updating parameters, after analyzing the abnormal signal and judging that the required updating parameter exists, the server system 300 returns existing and satisfied updating parameter to the deciding process module 240 and the specification parameter module 220 instead of re-building the updating parameter.

In addition, in order to increase the accuracy of filtering the frequency domain signal 231 by the filter module filter, a training module 260 and a coefficient data base 270 may be added. The training module 260 analyzes a filtering result of the frequency domain signal 231, so as to generate an adjusting value. Then, the training module 260 stores the filtering result and the adjusting value in the coefficient data base 270, such that the deciding process module 240 pre-corrects all the decision parameters 241 with reference to each of the adjusting values of the coefficient data base 270. Alternatively, when selecting the decision parameters 241, the deciding process module 240 corrects all the decision parameters 241 with reference to each of the adjusting values of the coefficient data base 270.

Next, the digital filtering system 200 further includes an expert system 280, which stores reference opinion of medical or care experts, so as to analyze whether the filtering result stored by the coefficient data base 270 is correct or not, and to adjust the adjusting values according to the analyzing result. Alternatively, the expert system 280 provides an inspecting platform, for the medical or care experts to manually inspect the accuracy of the filtering result, so as to adjust the relevant adjusting values.

In addition, the digital filtering system 200 further includes a recording module 290, which records an initial value and a current adjusting value of the digital filtering system 200, to avoid the issue such that the digital filtering system 200 may not return to the initial state after being adjusted. When the deciding process module 240 judges the decision parameters 241, it may similarly correct the decision parameters 241 together with the training module 260 with reference to the adjusting numerical value of the recording module.

Figure 2:
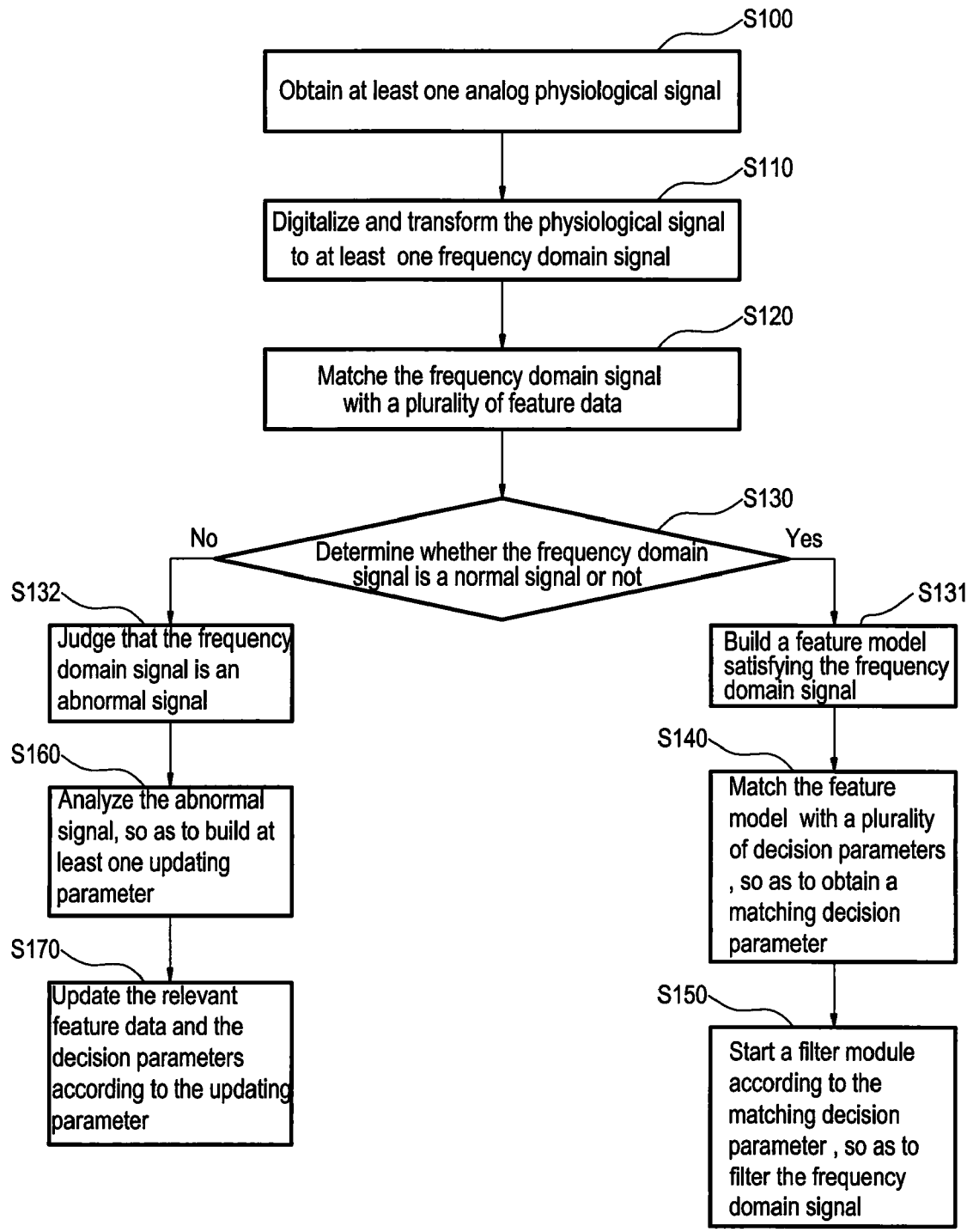
FIG. 2 is a flow chart of a digital filtering method according to the embodiment of the present invention.

Referring to FIG. 2, a flow chart of a digital filtering method according to the embodiment of the present invention is shown. For better understanding, please refer to FIG. 1 at the same time. The digital filtering method is applied to the digital filtering system 200 of FIG. 1, and the method includes the steps as follows.

Figure 3A:
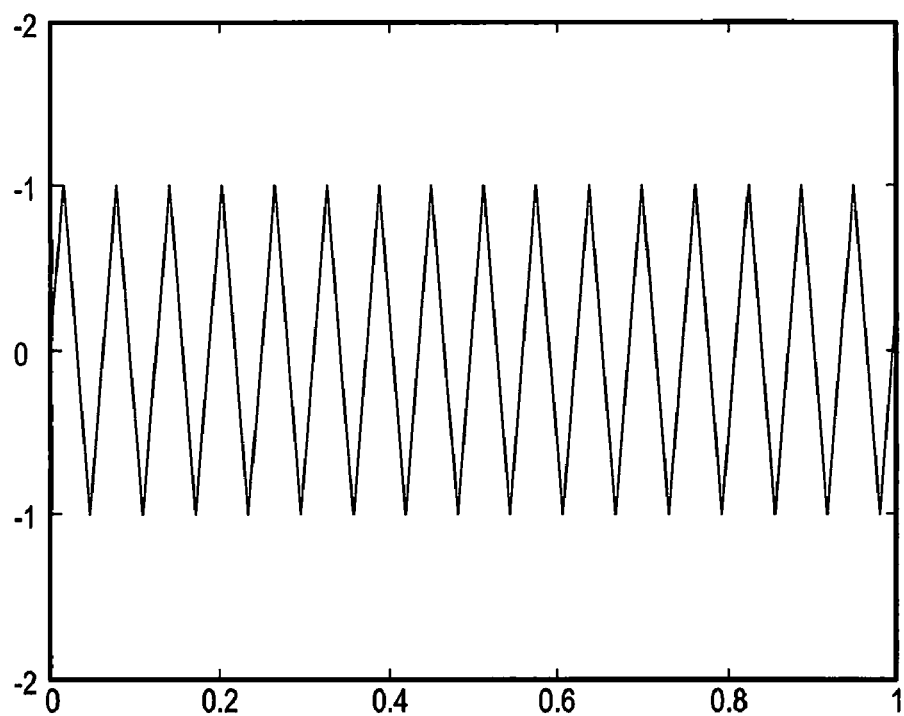
FIG. 3A is a schematic view of a ideal physiological signal according to the embodiment of the present invention.
Figure 3B:
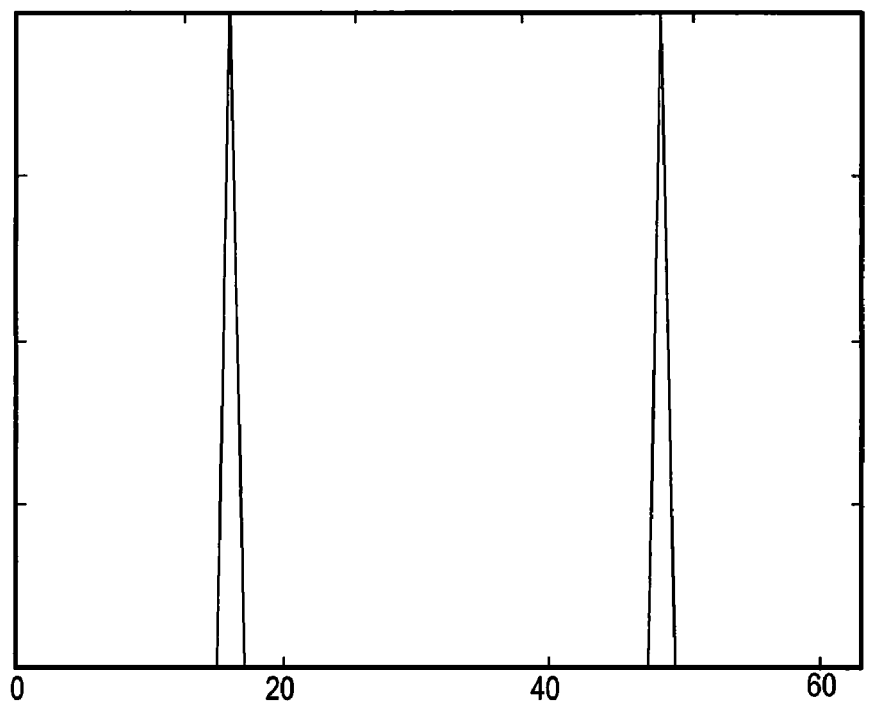
FIG. 3B is a schematic view of a ideal frequency domain signal according to the embodiment of the present invention.

At least one sensor 100 obtains at least one analog physiological signal (Step S100), and then a quantizing module 210 transforms the physiological signal to at least one frequency domain signal 231 (Step S110). As shown in FIGS. 3A and 3B, from the ideal perspective, under the environment of no noise, the physiological signal measured by the sensor 100 is a cyclic, orderly, and continuous analog signal as shown in FIG. 3A. As shown in FIG. 3B, the frequency domain signal 231 generated by digitalizing and performing the time-frequency transform on the ideal physiological signal according to the Fourier transform rule may be converged to the two most concentrated numerical values being approximately 18 HZ and with an intensity of 4 db, and being approximately 48 Hz and with an intensity of 4 db (as a descriptive example, and it is subject to the practical measurement).

Figure 4A:
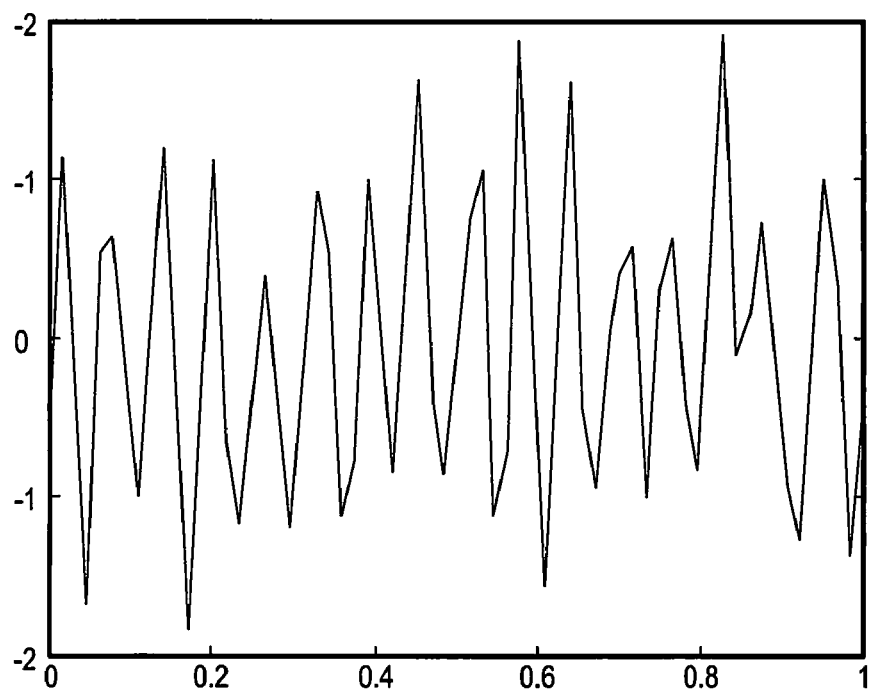
FIG. 4A is a schematic view of a practical physiological signal according to the embodiment of the present invention.
Figure 4B:
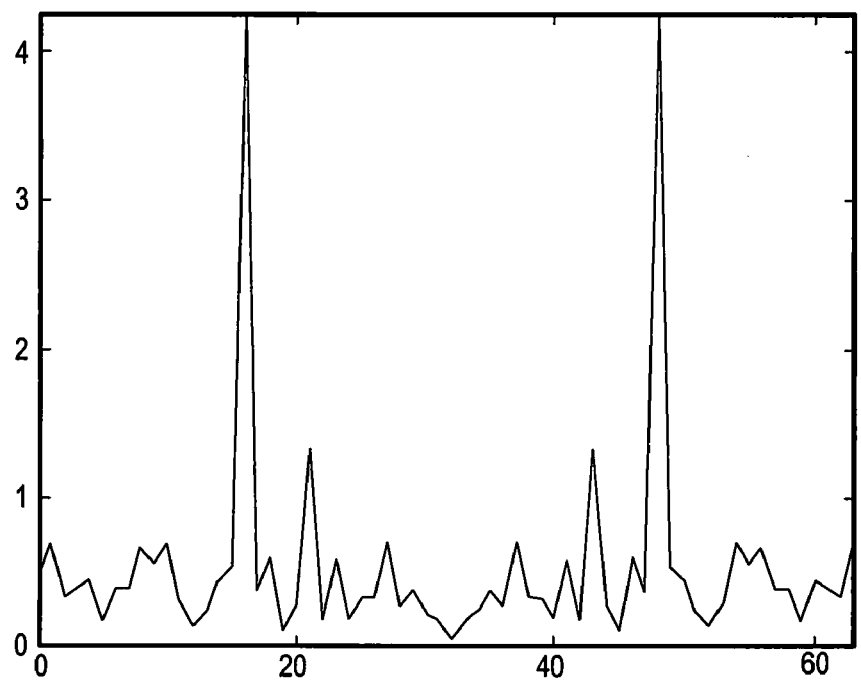
FIG. 4B is a schematic view of a practical frequency domain signal according to the embodiment of the present invention.

Practically, as shown in FIG. 4A, the physiological signal measured by the sensor 100 is mostly mixed with the noise (the source of the noise is as described above, and is not repeated), therefore after the time-frequency transform is performed, the generated frequency domain signal 231 is relatively divergent, as shown in FIG. 4B. Hereinafter, the frequency domain signal 231 generated by the physiological signal mixed with the noise is used for description.

Figure 5:
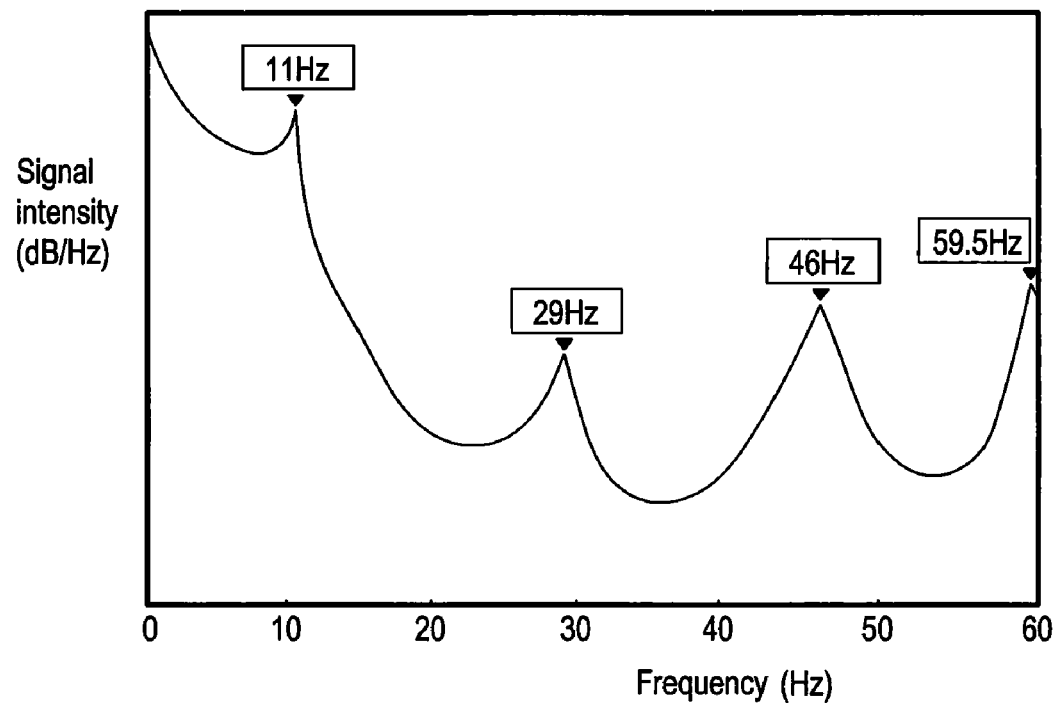
FIG. 5 is a schematic view of waveform turning points according to the embodiment of the present invention.

A specification parameter module 220 matches the frequency domain signal 231 with a plurality of feature data (Step S120). As described above, the specification parameter module 220 analyzes the type, the shape, and other features of the frequency domain signal 231 according to pre-built class data, waveform data, and unit parameter. As shown in FIG. 5, the specification parameter module 220 may firstly determine all the waveform turning points (marked by inverted triangles) of the frequency domain signal 231, then select a signal retrieving scope according to the waveform turning points, and determine the signal intensity corresponding to each waveform turning point, the spread spectrum width density of each waveform turning point after the waveform retrieving, the power density and the waveform of each frequency domain signal 231 on the spectrum, and other interval features. The specification parameter module 220 compares the analyzed numerical values with the feature parameters one by one, so as to obtain the matching feature parameter.

Then, the specification parameter module 220 determines whether the frequency domain signal 231 is a normal signal or not according to the matching result (Step S130). When at least one feature data matches with the frequency domain signal 231, the specification parameter module 220 builds a feature model 232 satisfying the frequency domain signal 231 (Step S131). The feature model 232 includes all the feature parameters satisfying the frequency domain signal 231. As described above, in order to prevent the data loss, the feature model 232 and the frequency domain signal 231 may be stored in a register module 230 in advance.

A deciding process module 240 matches the feature model 232 with a plurality of decision parameters 241, so as to obtain a matching decision parameter 241 (Step S140). The decision parameters 241 stored by the deciding process module 240 form a decision tree structure, the decision parameters 241 are the leafs of the decision tree, and the conditions used to determine the traveling paths are the feature parameters. Therefore, the deciding process module 240 guides the feature model 232 in the decision tree, so as to calculate the decision parameter 241 most appropriate for the feature model 232.

A filter-Clustering management module 250 starts a filter module according to the matching decision parameter 241, so as to filter the frequency domain signal 231 (Step S150). As described above, the decision parameter 241 is selected by guiding the feature model 232 in the decision tree, so the filter starting data, the filter adjusting parameter, and the operation power adjusting parameter in the decision parameter 241 definitely meet the demand of the feature model 232 and the frequency domain signal 231. Therefore, after the started filter module is adjusted by the selected filter adjusting parameter, the filtering result of the frequency domain signal 231 must be the most satisfying one required by the user. Further, the filter-Clustering management module 250 adjusts the circuit power of the whole digital filtering system 200 according to the operation power adjusting parameter, such that the digital filtering system 200 is in the most appropriate operating state, thereby lowering the circuit noise thereof. However, the filter adjusting parameter may be a high-pass parameter, a low-pass parameter, a band pass parameter, or a band rejection parameter.

On the contrary, when judging that the frequency domain signal 231 does not satisfy any feature data, the specification parameter module 220 judges that the frequency domain signal 231 is an abnormal signal (Step S132). That is to say, the frequency domain signal 231 is a signal through which the feature model 232 cannot be determined.

A server system 300 analyzes the abnormal signal, so as to build at least one updating parameter (Step S160). The abnormal signal may be transmitted to the server system 300 by the specification parameter module 220, the server system 300 analyzes the abnormal frequency domain signal 231 and builds an updating parameter satisfying the frequency domain signal 231. The updating parameter may include the decision parameters 241, feature parameters, and the traveling paths of the decision tree.

Figure 6:
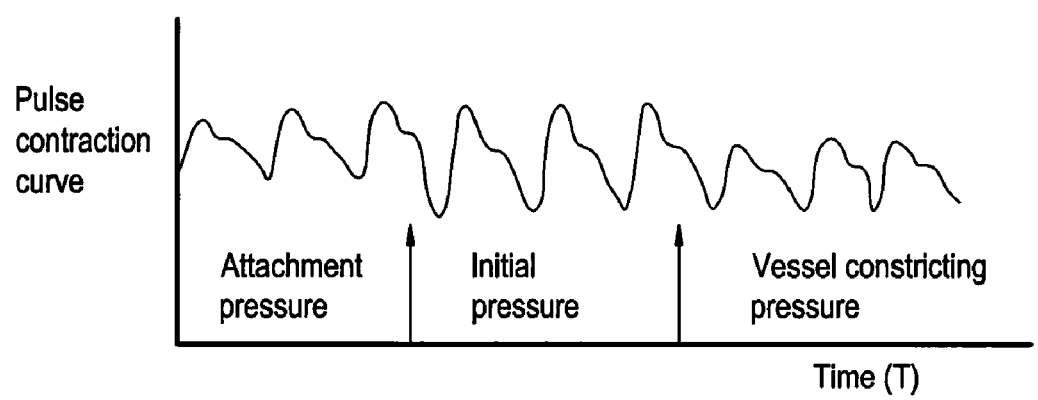
FIG. 6 is a schematic view of a pulse curve according to the embodiment of the present invention.
Figure 7:
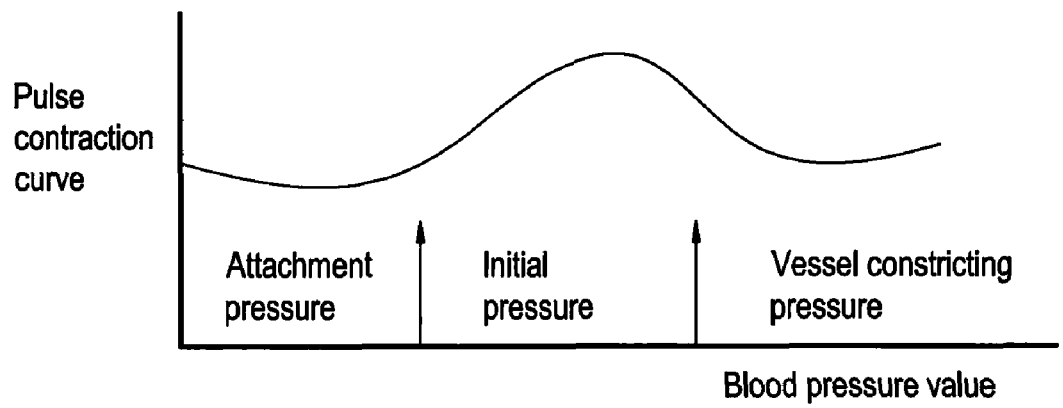
FIG. 7 is a schematic view of a blood pressure curve according to the embodiment of the present invention.

Finally, the server system 300 updates the feature data of the specification parameter module 220 and the decision parameters 241 of the deciding process module 240 according to the updating parameter (Step S170). It is assumed that currently the user measures the pulse curve, and the curve is as shown in FIG. 6. At the beginning, the digital filtering system 200 analyzes the frequency domain signal 231 of an attachment pressure. However, after continuously analyzing the continuous physiological signal, the digital filtering system 200 determines that the pulse curve of FIG. 6 has hidden values of initial pressure and vessel constricting pressure, and Step 100 to Step S150 are re-executed, so as to build a new feature model 232, derive new decision parameters 241, and thereby obtaining the continuous curve of the blood pressure as shown in FIG. 7 by the use of the new filter module and filter adjusting parameter. Alternatively, it is judged that the features parameters of the frequency domain signal 231 may not be obtained by matching, Step S100 to Step S170 are re-executed, so as to build new feature parameters, decision parameters 241, and the decision tree, thereby similarly obtaining the continuous curve of the blood pressure as shown in FIG. 7.

In addition, in order to increase the accuracy of filtering result, the filtering result may be guided in a training module 260. The training module 260 analyzes the filtering result of the frequency domain signal 231, so as to generate an adjusting value stored in a coefficient data base 270. The deciding process module 240 corrects each decision parameters 241 and the decision tree with reference to the adjusting value of the coefficient data base 270. Alternatively, when selecting the decision parameters 241, the deciding process module 240 corrects the selecting path of the decision tree with reference to the adjusting value of the coefficient data base 270, so as to select the most appropriate decision parameter 241.

In addition, the physiological signal is a continuous analog signal, so the specification parameter module 220 continuously generates new feature models 232. However, in order to prevent occupying the operating resource, the error judgment may be performed at the parts as follows.

Figure 8:
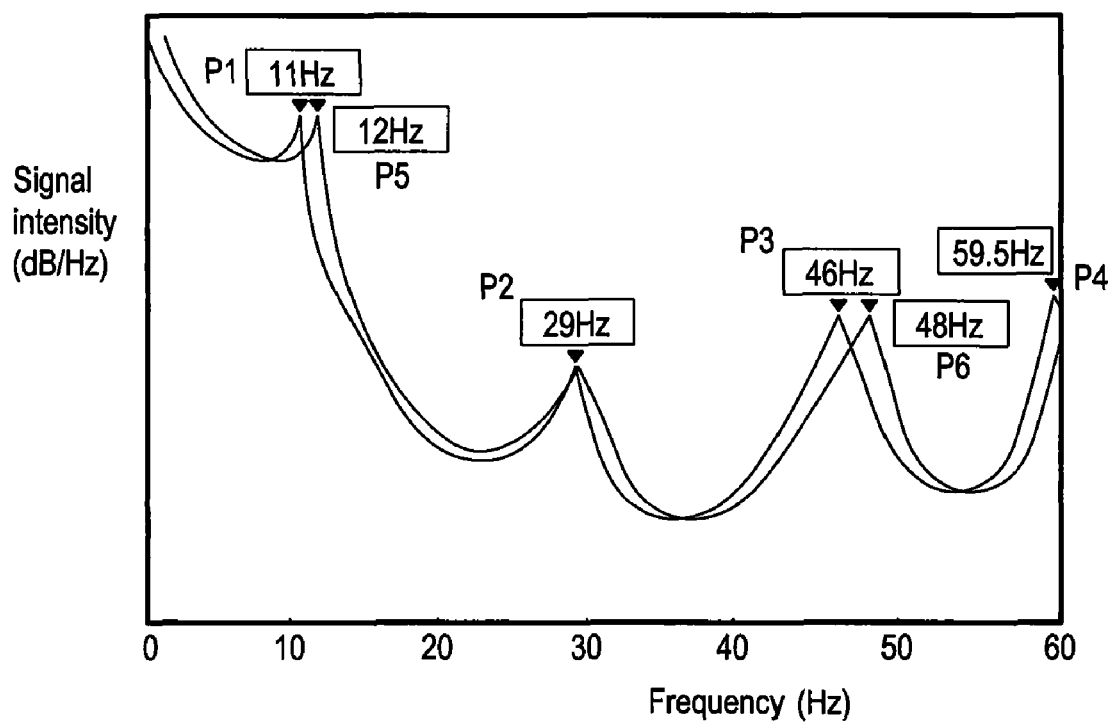
FIG. 8 is a schematic view of a comparison of feature models according to the embodiment of the present invention.

Firstly, when the difference of the feature models 232 generated by the specification parameter module 220 is not large, as shown in FIG. 8, the waveforms and the parameters of the feature models 232 are approximately the same, and the frequencies are slightly different, at this time, the specification parameter module 220 may use the same feature model 232.

Secondly, when the deciding process module 240 obtains the approximately same feature model 232, the same decision tree may be used.

Thirdly, when the training module obtains the approximately same filtering result, it is not necessary to re-calculate the adjusting value.

Figure 9:
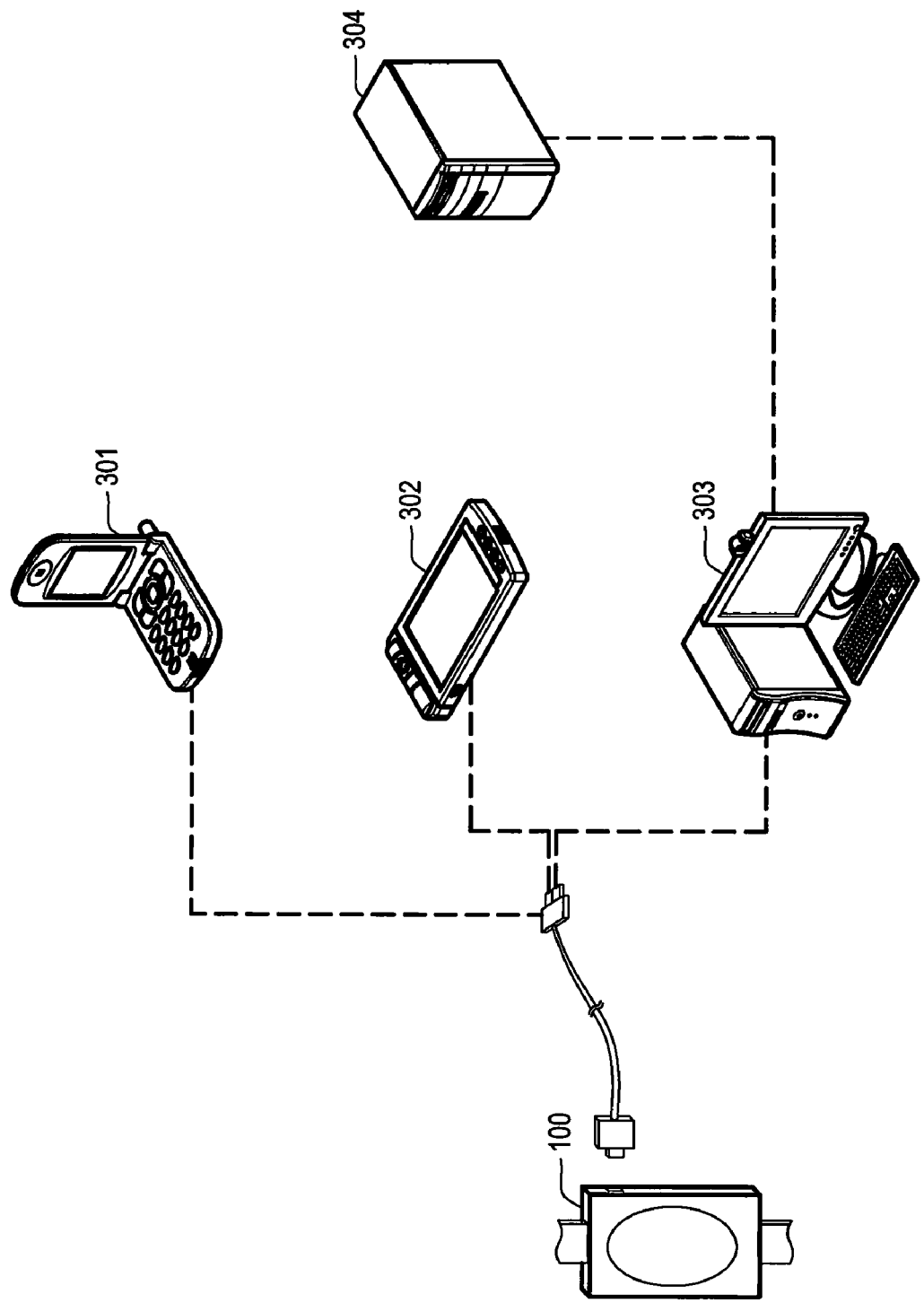
FIG. 9 is a schematic view of a system entity according to the embodiment of the present invention.

Referring to FIG. 9, a schematic view of a system entity according to the embodiment of the present invention is shown. The sensor 100 may be worn on the user's body, and the modules of the digital filtering system 200 except for the sensor 100 may be realized by programs, so as to be stored in an electronic device such as a 3G mobile phone 301, a personal digital assistant 302, a computer 303. Further, the server system 300 may be independent to form a back-end server 304.

The sensor 100 and the electronic device may be connected in a wired or a wireless manner. The wireless manner is, for example, blue tooth, infrared ray, Wi-max, zigbee, and other wireless network types. Similarly, the electronic device and the back-end server 304 may similarly communicate with each other in the manner of telecommunication or network, such as Wi-max and zigbee.

Figure 10:
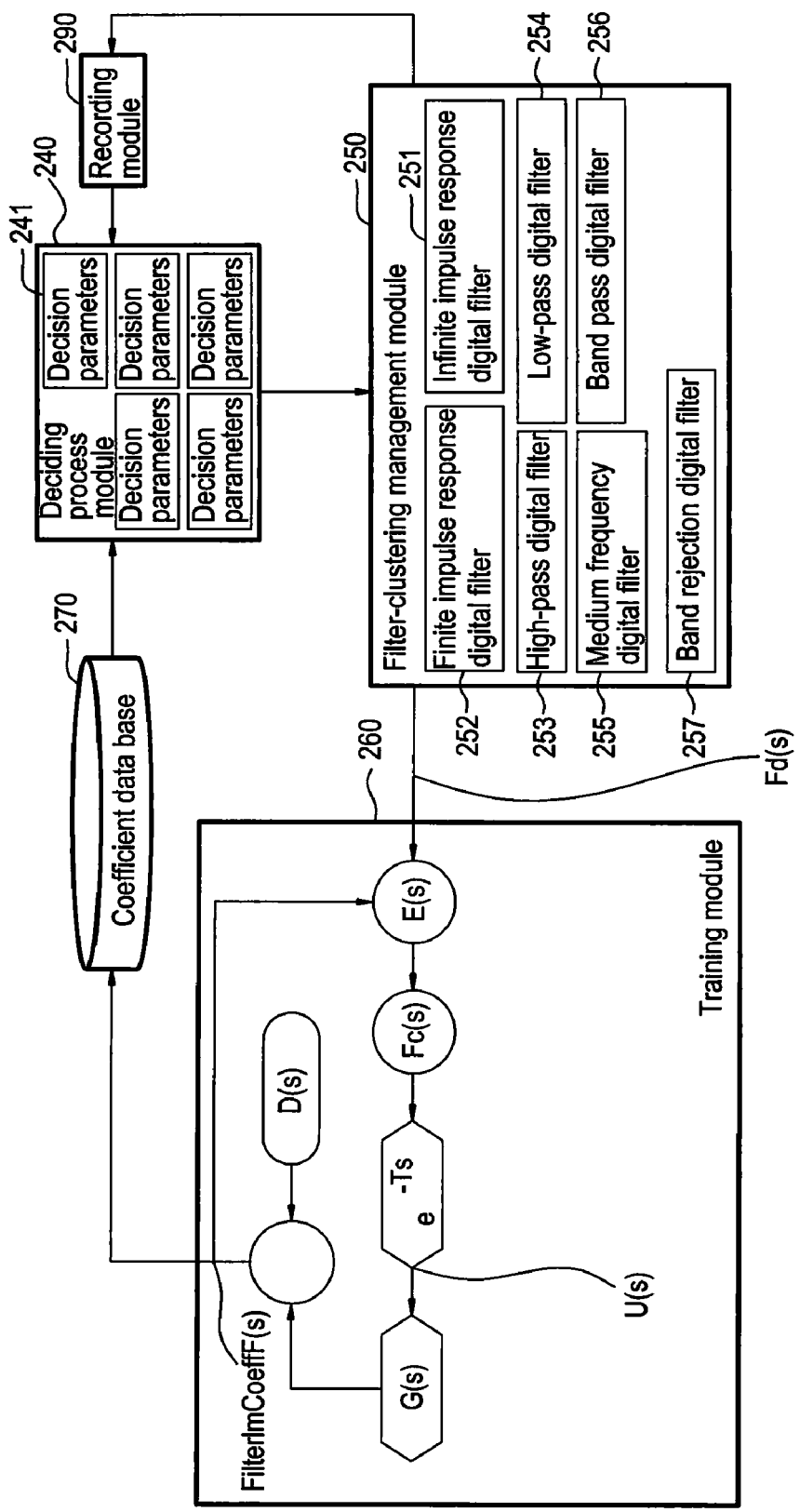
FIG. 10 is a schematic view of a function training according to the embodiment of the present invention.

Referring to FIG. 10, a function regulation schematic view of the training modules 260 training signals according to the embodiment of the present invention is shown.

In this assumption, Fd(s) presents the actual signal after the filter-Clustering management module 250 filtering. FilterImCoeffF(s) presents the desired output of a user. D(s) presents the limited condition coefficient from the external unknown interference factors. D(s) Fd(s), and FilterImCoeffF (s) are the signals having the same period T. U(s) is a control modulation parameter from an external input or from pre-set control modulation parameters. G(s) are the control system transfer function of the feedforward compensation and the feedback compensation.

The function block diagram of the FIG. 10 can be expressed as the following formula:

$$\text{FilterImCoeffF}(s) = G(s)\, U(s) + D(s)$$

$$U(s) = e^{-Ts}[U(s) + E(s)]$$

$$E(s) = Fd(s) - \text{FilterImCoeffF}(s)$$

By the above-mentioned formula, it can derive:

$$E(s) = e^{-Ts}[1 - G(s)]E(s) + Fd0(s)$$

wherein, Fd0(s) equivalent to the expected output, ie:

$$Fd0(s) = (1 - e^{-Ts})[Fd(s) - D(s)]$$

The training module 260 carries out the aforementioned operations of the actual output Fd(s) and FilterImCoeffF(s)

by the formula after the act of filtering, in order to achieve a repeat of the self-training, leading to the error convergence conditions or the stability conditions of the overall filter system.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A digital filtering system, comprising:
   at least one sensor, each providing an analog physiological signal;
   a quantizing module, for digitalizing and performing a time-frequency transformation on the physiological signal, so as to transform the physiological signal to at least one frequency domain signal;
   a specification parameter module, for storing a plurality of feature data, matching the frequency domain signal with the feature data, so as to obtain at least one feature data by matching and build a feature model of the frequency domain signal, and judging that the frequency domain signal is an abnormal signal and outputting the abnormal signal when the frequency domain signal does not satisfy any feature data;
   a deciding process module, for storing a plurality of decision parameters, and outputting a matching decision parameter of the feature model, wherein the decision parameters stored by the deciding process module form a decision tree structure, the decision parameters are the leafs of the decision tree, and the conditions used to determine the traveling paths are the feature parameters, and the deciding process module guides the feature model in the decision tree, so as to calculate the matching decision parameter most appropriate for the feature model;
   a filter-Clustering management module, comprising a plurality of filter modules, for starting a filter module according to the matching decision parameter, the filter module being used to filter the frequency domain signal; and
   a server system, for obtaining the abnormal signal, analyzing the abnormal signal to build at least one updating parameter, and updating the feature data of the specification parameter module and the decision parameters of the deciding process module.

2. The digital filtering system according to claim 1, wherein the quantizing module transforms the physiological signal to the frequency domain signal according to Fourier transform rule.

3. The digital filtering system according to claim 1, wherein each feature data comprises a class data, a waveform data, and a unit parameter.

4. The digital filtering system according to claim 3, wherein the unit parameter is selected from a group consisting of a signal retrieving scope, a signal intensity data, a spread spectrum width and density data, and an interval feature data.

5. The digital filtering system according to claim 1, wherein each decision parameter comprises a filter starting data, at least one filter adjusting parameter, and an operation power adjusting parameter of the digital filtering system.

6. The digital filtering system according to claim 5, wherein the filter adjusting parameter is a high-pass parameter, a low-pass parameter, a band pass parameter, or a band rejection parameter.

7. The digital filtering system according to claim 1, wherein the filter modules comprise a finite impulse response digital filter, an infinite impulse response digital filter, a high-pass digital filter, a low-pass digital filter, a medium frequency digital filter, a band pass digital filter, or a band rejection digital filter.

8. The digital filtering system according to claim 1, wherein the server system pre-stores a plurality of updating parameters, after the server system analyzes the abnormal signal and judges that the required updating parameter exists, the server system outputs the existing updating parameter.

9. The digital filtering system according to claim 1, further comprising a training module and a coefficient data base, wherein the training module analyzes a filtering result of the frequency domain signal, generates an adjusting value, and stores the filtering result and the adjusting value in the coefficient data base, the deciding process module corrects the decision parameters with reference to each of the adjusting values of the coefficient data base.

10. The digital filtering system according to claim 9, further comprising an expert system, for analyzing and correcting each of the adjusting values of the coefficient data base.

11. The digital filtering system according to claim 9, further comprising a recording module, for recoding a system initial value and a current adjusting value of the digital filtering system.

12. The digital filtering system according to claim 1, wherein the physiological signal is a continuous analog signal.

13. A digital filtering method, comprising:
   obtaining at least one analog physiological signal by at least one sensor;
   transforming the physiological signal to at least one frequency domain signal by a quantizing module;
   matching the frequency domain signal with a plurality of feature data by a specification parameter module;
   building a feature model satisfying the frequency domain signal by the specification parameter module, when at least one feature data matches with the frequency domain signal;
   matching the feature model with a plurality of decision parameters by a deciding process module, so as to obtain a matching decision parameter, wherein the decision parameters stored by the deciding process module form a decision tree structure, the decision parameters are the leafs of the decision tree, and the conditions used to determine the traveling paths are the feature parameters, and the deciding process module guides the feature model in the decision tree, so as to obtain the matching decision parameter most appropriate for the feature model;
   starting a filter module by a filter-Clustering management module according to the matching decision parameter, so as to filter the frequency domain signal;
   judging that the frequency domain signal is an abnormal signal, when the frequency domain signal does not satisfy any feature data; and
   analyzing the abnormal signal by a server system, so as to build at least one updating parameter, and updating the feature data of the specification parameter module and the decision parameters of the deciding process module according to the updating parameter.

14. The digital filtering method according to claim 13, after filtering the frequency domain signal, further comprising:
   analyzing a filtering result of the frequency domain signal, and generating an adjusting value; and
   correcting each of the decision parameters according to the adjusting value.

15. The digital filtering method according to claim 13, wherein the quantizing module transforms the physiological signal to the frequency domain signal according to Fourier transform rule.

16. The digital filtering method according to claim 13, wherein each feature data comprises a class data, a waveform data, and a unit parameter.

17. The digital filtering method according to claim 16, wherein the unit parameter is selected from a group consisting of a signal retrieving scope, a signal intensity data, a spread spectrum width and density data, and an interval feature data.

18. The digital filtering method according to claim 13, wherein each decision parameter comprises a filter starting data, at least one filter adjusting parameter, and an operation power adjusting parameter of the digital filtering system.

19. The digital filtering method according to claim 18, wherein the filter adjusting parameter is a high-pass parameter, a low-pass parameter, a band pass parameter, or a band rejection parameter.

20. The digital filtering method according to claim 13, wherein the quantizing module digitalizes and performs a time-frequency transformation on the physiological signal according to the Fourier transform rule, so as to transform the physiological signal to the frequency domain signal.

21. A non-transitory recording medium of digital filtering, recording computer-readable computer program codes, the non-transitory recording medium encoding with computer program codes which is executed by a computer to perform a method of digital filtering, comprising:
   obtaining at least one analog physiological signal;
   digitalizing and transforming the physiological signal to at least one frequency domain signal;
   matching the frequency domain signal with a plurality of feature data;
   building a feature model satisfying the frequency domain signal, when at least one feature data matches with the frequency domain signal;
   matching the feature model with a plurality of decision parameters, so as to obtain a matching decision parameter, wherein the decision parameters stored by the deciding process module form a decision tree structure, the decision parameters are the leafs of the decision tree, and the conditions used to determine the traveling paths are the feature parameters, and the deciding process module guides the feature model in the decision tree, so as to obtain the matching decision parameter most appropriate for the feature model;
   starting a filter module according to the matching decision parameter, so as to filter the frequency domain signal;
   judging that the frequency domain signal is an abnormal signal, when the frequency domain signal does not satisfy any feature data; and
   analyzing the abnormal signal to build at least one updating parameter, and updating the feature data and the decision parameters according to the updating parameter.

22. The non-transitory recording medium of a digital filtering program according to claim 21, wherein after the frequency domain signal is filtered, the method further comprises:
   analyzing a filtering result of the frequency domain signal, and generating an adjusting value; and
   correcting each of the decision parameters according to the adjusting value.

23. The non-transitory recording medium of a digital filtering program according to claim 21, wherein the quantizing module transforms the physiological signal to the frequency domain signal according to Fourier transform rule.

24. The non-transitory recording medium of a digital filtering program according to claim 21, wherein each feature data comprises a class data, a waveform data, and a unit parameter of the frequency signal.

25. The non-transitory recording medium of a digital filtering program according to claim 24, wherein the unit parameter is selected from a group consisting of a signal retrieving scope, a signal intensity data, a spread spectrum width and density data, and an interval feature data.

26. The non-transitory recording medium of a digital filtering program according to claim 21, wherein each decision parameter comprises a filter starting data, at least one filter adjusting parameter, and an operation power adjusting parameter of the digital filtering system.

27. The non-transitory recording medium of a digital filtering program according to claim 26, wherein the filter adjusting parameter is a high-pass parameter, a low-pass parameter, a band pass parameter, or a band rejection parameter.

28. The non-transitory recording medium of a digital filtering program according to claim 21, wherein the step of digitalizing and transforming the physiological signal to at least one frequency domain signal comprises:
   digitalizing the physiological signal; and
   performing a time-frequency transformation on the digitalized physiological signal according to the Fourier transform rule, so as to transform the physiological signal to the frequency domain signal.

* * * * *